United States Patent [19]

Lauritzen

[11] Patent Number: 4,622,089
[45] Date of Patent: Nov. 11, 1986

[54] METHOD OF MAKING BLISTER PAD ADHESIVE BANDAGE

[75] Inventor: Nels J. Lauritzen, Piscataway, N.J.

[73] Assignee: Johnson & Johnson Products, Inc., New Brunswick, N.J.

[21] Appl. No.: 726,170

[22] Filed: Apr. 22, 1985

Related U.S. Application Data

[62] Division of Ser. No. 470,417, Feb. 28, 1983, abandoned.

[51] Int. Cl.⁴ .................. A61L 15/00; B32B 31/18; B32B 31/20
[52] U.S. Cl. .................. 156/250; 156/251; 156/289; 156/290; 156/324; 128/155; 128/156; 128/169
[58] Field of Search ............. 156/62.8, 196, 199, 156/251, 290, 300, 324, 582, 583.1, 289; 128/155, 156, 169; 428/91, 198, 400

[56] References Cited

U.S. PATENT DOCUMENTS

| | | | |
|---|---|---|---|
| 2,340,142 | 1/1944 | Rauner | 604/306 |
| 2,521,985 | 9/1950 | Lang et al. | 156/62.8 |
| 3,468,096 | 9/1969 | Franz | 156/290 |
| 3,794,537 | 2/1974 | Rahmes | 156/62.8 |
| 3,900,027 | 8/1975 | Keedwell | 128/268 |
| 3,998,988 | 12/1976 | Shimomai | 428/400 |
| 4,103,054 | 7/1978 | Okamoto | 428/91 |
| 4,126,130 | 11/1978 | Cowden et al. | 128/156 |
| 4,136,221 | 1/1979 | Okamoto | 428/91 |
| 4,140,677 | 2/1979 | Uno | 528/322 |
| 4,219,019 | 7/1980 | Coates | 128/156 |
| 4,287,251 | 9/1981 | King | 428/198 |
| 4,530,353 | 7/1985 | Lauritzen | 128/156 |

Primary Examiner—Caleb Weston
Attorney, Agent, or Firm—Wayne R. Eberhardt

[57] ABSTRACT

Adhesive bandages comprising a blister pad and adjacent adhesive-coated areas are prepared from heat-fusible bandage materials, preferably a nonwoven batt material, by applying the pad material to a base material and heat-welding around the perimeter of the pad to totally enclose the interior thereof. The portions of the base material extending from the pad area are compacted under heat and pressure to provide a surface suitable for a coating with adhesive. A medicated gel or other therapeutic material may be included within the confines of the pad area to provide a medicated blister bandage.

16 Claims, 9 Drawing Figures

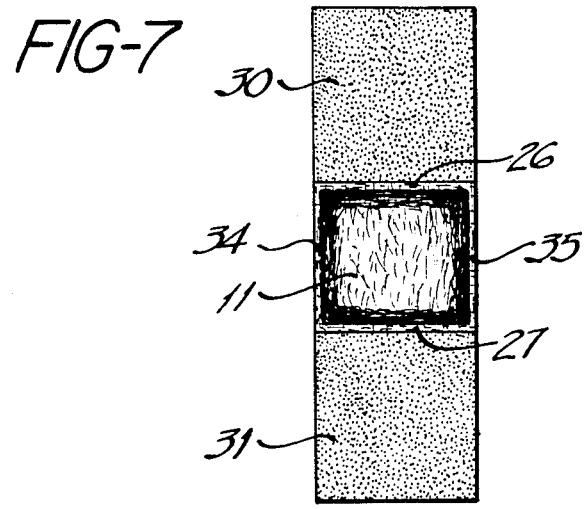
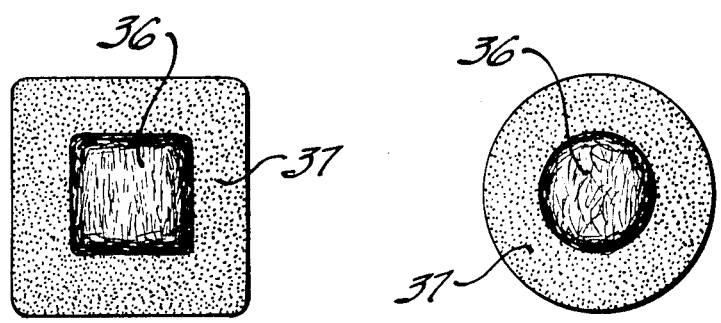

4,622,089

METHOD OF MAKING BLISTER PAD ADHESIVE BANDAGE

This application is a division of application Ser. No. 470,417, filed Feb. 28, 1983, abandoned.

FIELD OF INVENTION

The present invention relates to adhesive bandages comprising a central pad area and adjacent adhesive areas, and more particularly, to blister pad adhesive bandages constructed entirely from heat-fusible, nonwoven fabric materials.

BACKGROUND OF THE INVENTION

Adhesive bandages comprising a central pad area and adjacent adhesive areas are well-known in the art and popular as first aid wound dressings. Current bandages generally comprise an elongated strip of cloth or plastic backing material coated on one surface with a pressure sensitive adhesive. A gauze or sponge pad is secured to the adhesive surface in a central location to serve as the wound cover. The wound facing surface of the pad may be plastic-coated or otherwise treated to prevent the pad from adhering to the wound. Plastic-coated release strips are placed over the adhesive areas and the entire assembly is placed in a sealed package and sterilized to be ready for use.

An alternate form of adhesive bandage, generally referred to as an island bandage, comprises a generally square, round or oval adhesive coated backing material with a centrally located pad forming an island surrounded by the adhesive surface. The adhesive surface is similarly covered by release paper before the bandage is packaged and sterilized.

The adhesive bandages of the prior art are characterized by their construction of two basic components—the adhesive coated backing material and the wound covering pad material. The pad material may be dry or impregnated with various bactericides or other wound treatment medicaments. The capacity of the pad to absorb and hold such compositions is a limiting factor on the amount of such material which may be incorporated into the bandage.

It is an object of the present invention to provide an improved adhesive bandage. It is a further object of this invention to provide a low cost adhesive bandage through the use of inexpensive materials and low cost manufacturing techniques. A further object of this invention is to provide an adhesive bandage having a high loading of wound treatment medicament in the pad area. These and other objects of the present invention will be apparent from the ensuing description and claims of the invention.

SUMMARY

Adhesive bandages comprising an elongated strip of material having a centrally-located blister pad and adjacent adhesive portions extending from each side of the pad area are prepared from a heat-bondable, absorbent, nonwoven fabric material. The blister pad is applied to the center of the bandage strip and secured by heat bonding. A medicated gel or other material may be deposited on the bandage strip and covered with the blister pad to provide a medicated bandage. The portions of the bandage extending beyond the pad area are permanently compacted to provide a surface suitable for coating with adhesive. The pad area is preferably left uncompacted to retain loft and absorbency, but may be heat glazed to provide a nonadhering wound release surface.

Strip bandages are conveniently prepared according to the present invention from a first, continuous base-fabric having a width equal to the overall length of the desired bandage, and a second, continuous pad-fabric having a width at least equal to the desired pad area. The base fabric is fed through a station where a medicated gel or other material is deposited onto the center of the moving fabric if desired. The pad fabric is then applied as a blister dome over the deposited material and the combined fabrics passed through a hot roll calendering station where the edges of the pad and the portions of the base fabric extending from each side of the pad area are compacted and heat-fused to secure the pad and to form a dense, nonwoven sheet-like structure extending from the pad area.

The composite fabric is next passed through an adhesive application station where a pressure-sensitive adhesive, preferably a hot melt-type adhesive, is coated onto one surface of the compacted base fabric on either side of the pad area. Adhesive release liners are applied over the adhesive area and the composite structure fed to a cutting station where strips are cut or stamped transversely to machine direction of the web to obtain individual adhesive bandages. As the bandages are cut from the composite web, the edges of the pad area are heat-sealed along a narrow band to form a well-defined pad area which totally encloses the deposited material. The resulting bandages are ready to be packaged and sterilized.

Island bandages according to the present invention are prepared by depositing the medicated gel onto the center of the base fabric in spots spaced at intervals in registry with the desired pad area of the final bandage. The pad fabric, preferably of the same width as the base fabric, is applied and the combined fabrics passed through an embossing station where the fabric surrounding the pad area is compacted and heat-fused to form a central blister pad surrounded by a compacted, nonwoven sheet-like structure.

The adhesive is applied to the compacted portion of the bandage fabric by printing or other suitable means. Adhesive release liners are applied over the adhesive-coated areas and the bandages die cut to form individual island bandages having a central blister pad area. The resulting bandages are packaged and sterilized using conventional procedures.

The material used in the fabrication of bandages according to the present invention is preferably a nonwoven fabric composed of absorbent fibers such as cellulose or rayon and heat-fusible fibers such as polyethylene or polypropylene, in relative proportions such that the pad of the finished bandage is soft and absorbent while the heat bonded and compacted areas are strong and stable.

DESCRIPTION OF DRAWINGS

FIG. 7 is a top plan view from the pad side of a strip adhesive bandage according to the present invention, with the adhesive release strips removed.

FIG. 8 is a top plan view from the pad side of a square island adhesive bandage according to the present invention, with the adhesive release strips removed.

FIG. 9 is a top plan view from the pad side of a spot adhesive bandage according to the present invention, with the adhesive release strips removed.

DETAILED DESCRIPTION OF THE INVENTION

Figure 1:
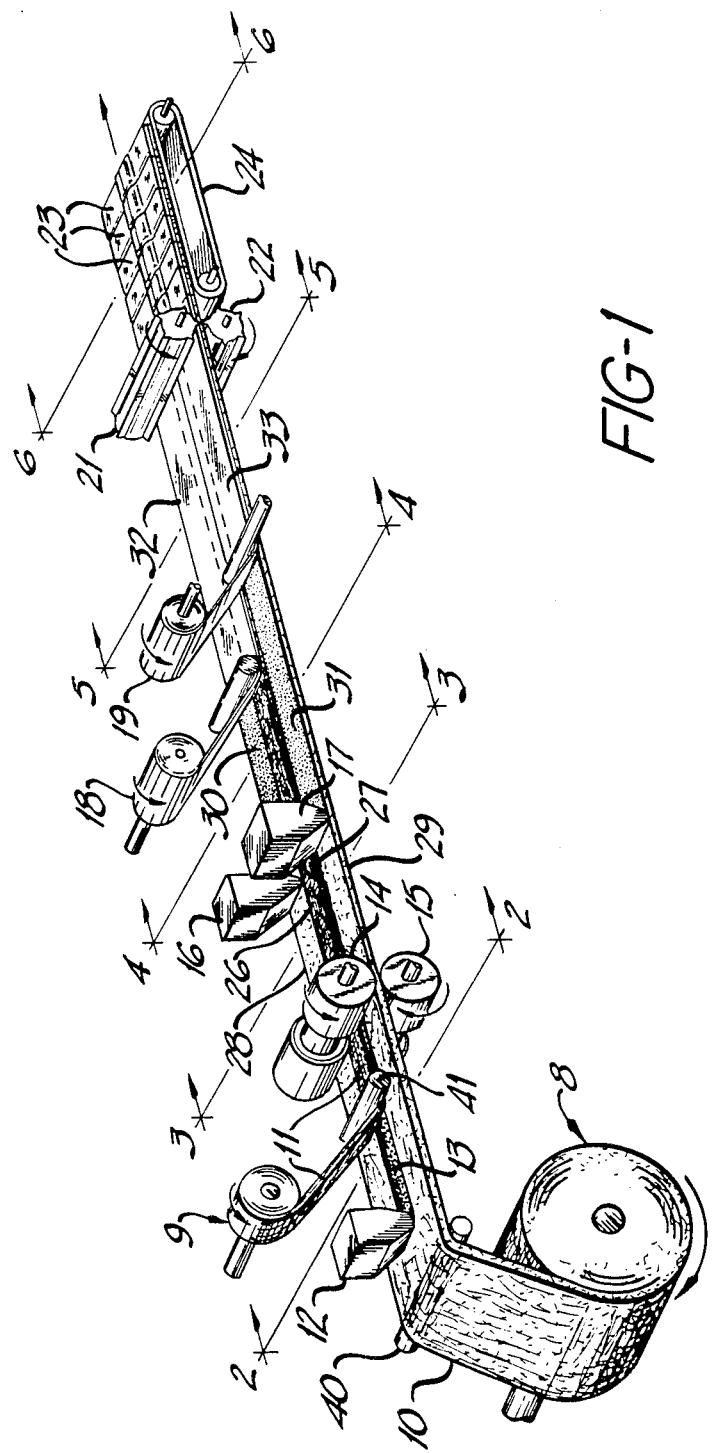
FIG. 1 is schematic representation in perspective of a process used to produce strip adhesive bandages of the present invention.

The strip adhesive bandages of the present invention are fabricated from continuous lengths of bandage material which are preferably bulky, heat-fusible, absorbent, nonwoven fabrics. The bandage is fabricated by positioning the pad material over the center area of the base fabric, securing the pad by heat welding the edges thereof, and heat fusing the portions of the base fabric extending from the pad area to provide surfaces capable of accepting an adhesive. After applying the adhesive and covering the adhesive surfaces with release liners, the composite web is cut transversely to its machine direction in strips the width of the desired bandage.

The central pad portion of the bandage comprises a double thickness of the starting bandage materials. Since it is generally desirable for the bandage pad to be absorbent as well as providing a cushioning effect, it is important for the initial bandage materials to also possess these properties. In addition, since the fabric forming the pad must be secured in some manner, the bandage materials are preferably a heat-fusible composition which permits the pad fabric to be continuously and permanently heat-welded along the edges to the base fabric.

A bandage material meeting all the above requirements is a nonwoven fabric comprising a mixture of cellulose or other absorbent fibers and polyethylene or other heat-fusible fibers. The heat-fusible fibers are interspersed throughout the web and are preferably present in an amount of at least 10% by weight. The fabric preferably has sufficient thickness or bulk so that the triple-layered pad has a thickness of at least 2 mm in the final bandage. Nonwoven webs useful in the practice of the present invention are known in the art for use in other applications. See, for example, U.S. Pat. Nos. 2,774,128; 3,067,747; 4,083,913; 4,160,159; and 4,307,721.

A particularly preferred bandage material is a low density, highly absorbent, thermal bonded nonwoven fabric comprising absorbent fibers and staple length polyester-polyethylene conjugate fibers. These nonwoven fabrics are produced by a process which includes producing a web comprising absorbent fibers and staple length polyester/polyethylene conjugate fibers; subjecting the web to a temperature sufficient to fuse the lower melting component of the conjugate fibers without fusing the higher melting component while maintaining the web under little or no compression; and cooling the web to resolidify the lower melting component of the conjugage fibers, thereby forming a nonwoven fabric bonded at sites where the conjugate fibers touch each other and adjacent absorbent fibers.

A particularly preferred nonwoven fabric is a laminate comprising a core of a mixture of short-length natural cellulose fibers and staple length polyester/polyethylene conjugate fibers, and a light weight veneer of heat-fusible fibers on each surface of the core. The composite web is passed through a through-air heater to fuse the lower melting component of the conjugate fibers while maintaining the fibrous integrity of these fibers, and to fuse or soften the surfaces of the heat-fusible fibers in the two outer veneers. As the material emerges from the heater and cools, the fused surfaces of the lower melting component of the conjugate fibers, i.e., the polyethylene, solidify, and bonds form where these surfaces touch each other and other fibers.

The thermal-bonded, nonwoven fabrics particularly useful in the practice of the present invention employ polyester/polyethylene conjugate fibers wherein at least about 50 percent of the surface of the individual fibers is polyethylene. Most preferred are sheath/core fibers with the polyethylene as the sheath and the polyester as the core. The fibers will usually have a denier within the range of from about 1 to about 6, and a length within the range of from about $\frac{1}{2}$ inch to about 3 or 4 inches.

Absorbent fibers employed in such thermal-bonded, nonwoven fabrics include rayon staple fibers, cotton fibers, short length natural cellulose fibers such as wood pulp fibers and cotton linters, and mixtures thereof.

Heat-fusible fibers used in the veneer of the nonwoven fabric are preferably staple length conjugate fibers. However, if desired, other types of heat-fusible fibers such as polypropylene homofil fibers can be used in the veneer. The veneer can also contain other fibers, such as rayon, cotton, or polyester staple fibers.

The above bonded, nonwoven fabrics normally have basis weights from about $\frac{1}{2}$ to about 6 ounces per square yard. The bulk density of the fabrics is usually below about 0.15 gram per cubic centimeter, preferably below about 0.09 gram per cubic centimeter, e.g., from about 0.02 to about 0.09 gram per cubic centimeter, and more preferably, from about 0.025 to about 0.06 gram per cubic centimeter. The fabrics preferably have an absorbent capacity, as measured by a Gravimetric Absorbency Tester, of at least 600 percent and preferably at least 1400 percent, exclusive of any nonabsorbent layer such as a veneer of 100 percent fusible fibers.

Figure 2:
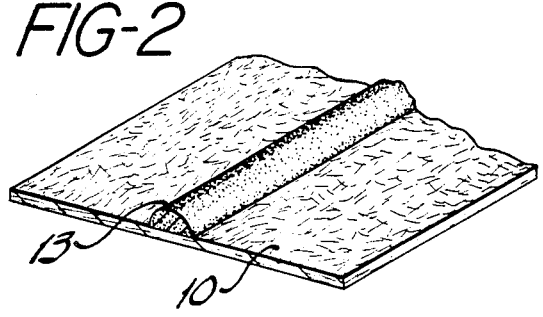
FIG. 2 is a cross-sectional view in perspective of the base web of FIG. 1 through line 2—2.
Figure 3:
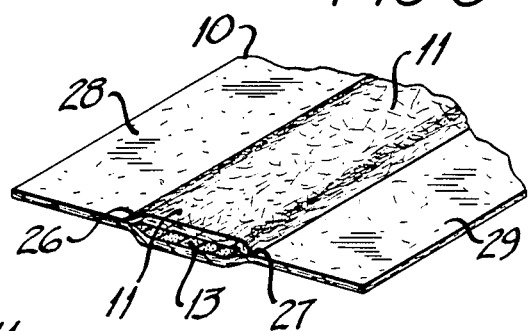
FIG. 3 is a cross-sectional view in perspective of the base web after application of the pad, through line 3—3 of FIG. 1.

The process of preparing adhesive strip bandages from continuous rolls of bonded, nonwoven fabric bandage material will be better understood by reference to FIGS. 1 through 6. In FIG. 1, the center portion of nonwoven base fabric 10 from roll 8 passes over idler roll 40 and under metering apparatus 12 where a bead or spots of medicated gel or other material 13 is deposited onto the center line of the fabric. The cross section of the base fabric carrying the gel is illustrated in FIG. 2. Nonwoven pad fabric 11 feeding from roll 9 passes under idler roll 41 which is adjusted to provide clearance for the gel between the pad and base fabrics. The composite fabric next passes between hot calendaring rolls 14 and 15 where the edges 26 and 27 of the pad fabric are welded to the base fabric and the side widths 28 and 29 of fabric extending from the pad area are compacted under heat and pressure to form a thin, dense, sheet-like material. Roll 14 includes a bridging center section to avoid compacting the pad area of the fabric. The cross section of the resulting product is illustrated in FIG. 3.

Figure 4:
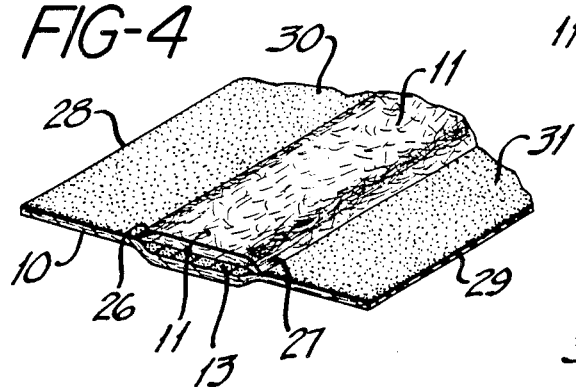
FIG. 4 is a cross-sectional view in perspective of the base web and pad after application of adhesive, through line 4—4 of FIG. 1.

The composite fabric next passes through the adhesive application station where a pressure-sensitive, skin-compatible adhesive is applied from reservoirs 16 and 17 to the compacted side portions of the material, the adhesive coating being designated as 30 and 31. FIG. 4 is a view in cross section of the adhesive-coated composite fabric. The adhesive may be any pressure-sensitive, medical grade adhesive suitable for use in adhesive bandages, and is preferably a hypoallergenic hot melt adhesive. Emulsion adhesives may also be used provided the adhesive application station includes means for drying the adhesive after application.

Figure 5:
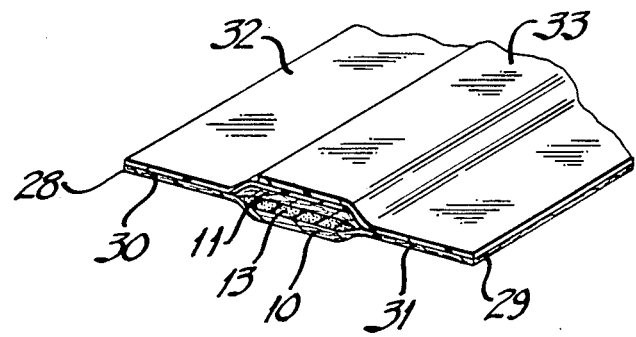
FIG. 5 is a cross-sectional view in perspective of the base web and pad of FIG. 4 after application of adhesive release papers, through line 5—5 of FIG. 1.
Figure 6:
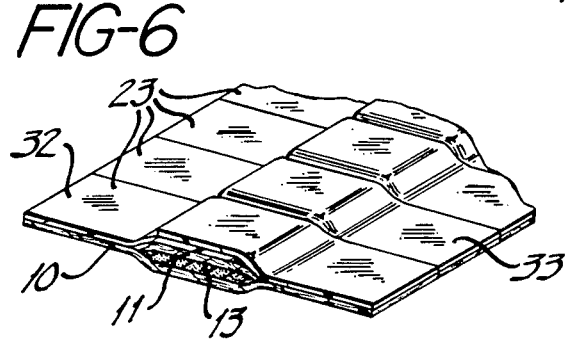
FIG. 6 is a cross-sectional view in perspective of the base web and pad of FIG. 5 after cutting into strips, through line 6—6 of FIG. 1.

As the adhesive-coated material continues through the process, the adhesive coating and the central pad area are covered by release papers 32 and 33 fed from rolls 18 and 19 respectively. The release papers preferably overlap along the center of the web over the pad area. FIG. 5 is a view in cross section of the composite material after application of the release papers.

The composite material next passes through a cutting station where cutters 21 and 22 cut the material into transverse strips 23 while simultaneously heat-fusing the cut edges of the pad fabric to enclose the gel material. The cut strips are carried on conveyor belt 24 to a packaging station (not shown) where individual strips are packaged in sealed envelopes prior to sterilization. The cut strips 23 are further illustrated in cross section in FIG. 6.

An individual strip bandage produced according to the present invention is illustrated in FIG. 7 with the adhesive release papers removed. In the illustrated bandage, pad 25 is set in from the longitudinal edges of the bandage by heat-fused areas 34 and 35 to form a well-defined pad portion which totally encloses the medicated gel or other material contained between the base fabric and the pad fabric.

Other bandage configurations and constructions utilizing the inventive concepts of the present invention will be apparent to those skilled in the art, the principle feature of the present invention being the construction of an adhesive bandage and pad utilizing heat-fusible bandage materials, preferably continuous webs comprising heat-fusible fibers.

Representative of such other bandage configurations are the square island bandage illustrated in FIG. 8 and the spot bandage illustrated in FIG. 9, both of which are herein referred to as island bandages. Island bandages are characterized by centrally located blister pad area 36 surrounded by an adhesive-coated area 37. To provide an adhesive area of uniform thickness throughout, it is desirable for the pad fabric used in the manufacture of the bandage to extend over the entire width of bandage rather than simply over the pad area as in the case of the strip bandage. Additionally, to prevent the medicated gel from interfering with compaction of the fabric and application of the adhesive, the gel is applied to the base fabric in spots in registry with the final pad area of the bandages.

The pad area of the island bandage is sealed by passing the fabrics through a hot embossing station, with rollers configured according to the size and shape of the desired bandage whereby the areas of the bandage surrounding the pad are heat-compacted to form a dense, sheet-like, structure capable of accepting an adhesive coating. The adhesive is preferably applied by transfer coating or other convenient method to provide a continuous coating of adhesive over the compacted material surrounding the pad area. Adhesive release liners are applied in continuous strips overlapping the central pad area, and individual bandages then die cut from the continuous feed of composite material.

Bandage flexibility and bias characteristics can be modified by altering fiber type and orientation. The bandage material can be further modified by incorporating fiber finishes to vary absorbency characteristics if desired. The surface of the pad intended for placement against the wound may be heat glazed or otherwise surface modified to provide wound release characteristics without significantly affecting the bulk or absorbency of the pad. These and other variations which will be apparent to those skilled in the art are included within the scope of the present invention.

What is claimed is:

1. A method for the continuous production of a plurality of adhesive strip bandages from a bulky heat-fusible, nonwoven material, said bandages comprising an elongated backing strip and a centrally positioned wound covering pad, said method comprising the steps of
   (a) providing a first continuous source of said material for said backing strip having a width corresponding to the desired length of the bandage,
   (b) providing a second continuous source of said material for said pad having a width at least equal to the desired length of said pad,
   (c) centering the width of the pad material on the width of the backing material,
   (d) securing the pad material to the backing material by compacting and heat-fusing said pad and backing materials along the edges of said pad material,
   (e) compacting and heat-fusing the portions of the backing material extending beyond the width of the pad to obtain a dense sheet-like structure,
   (f) applying a coating of a pressure-sensitive adhesive to one surface of said compacted portions of said backing,
   (g) covering said adhesive-coated surface with a release liner, and
   (h) cutting the resulting composite material into narrow strips across the width of the backing while simultaneously compacting and heat-fusing the pad and the backing along the cut edges thereof, whereby there are formed individual adhesive strip bandages comprising an adhesive coated backing strip and centrally located pad.

2. A method of claim 1 wherein a medicinal or therapeutic composition is deposited centrally on said backing material prior to centering and securing said pad material to said backing material.

3. A method of claim 1 wherein said edges of said pad material are secured to said backing material and said side portions of said backing material are compacted and heat-fused by compressing said bulky, nonwoven material while heated to about 100°–150° C.

4. A method of claim 1 wherein said nonwoven material comprises a mixture of absorbent fibers with at least 10% heat-fusible fibers.

5. A method of claim 4 wherein said heat-fusible fibers are staple length polyester core/polyethylene sheath conjugate fibers.

6. A method of claim 1 wherein said nonwoven material comprises a core of a mixture of absorbent fibers and heat-fusible polyester/polyethylene conjugate fibers, and an outer veneer on both faces of said core comprising a nonwoven web of heat-fusible polyester/polyethylene conjugate fibers.

7. A method of claim 6 wherein said absorbent fibers are selected from the group consisting of rayon, cotton, wood pulp, cotton linters, and mixtures thereof.

8. A method of claim 6 wherein the surface of said pad comprising a veneer of said heat-fusible fibers is heat-glazed to impart nonsticking, wound release properties to said pad.

9. A method for the continuous production of a plurality of adhesive island bandages from a bulky heat-fusible nonwoven material, said bandages comprising a central wound covering pad and a surrounding adhesive coated backing, said method comprising the steps of
 (a) providing a first continuous source of said material for said backing having a width corresponding to the desired length of the bandage,
 (b) providing a second continuous source of said material for said pad having a width at least equal to the desired length of the pad,
 (c) centering the width of the pad material on the width of the backing material,
 (d) securing the pad material to the backing material by compacting and heat-fusing those portions of the pad material and backing material which extend beyond the central pad area to obtain a dense sheet-like structure,
 (e) applying a coating of pressure-sensitive adhesive to one surface of said compacted portions of said pad and base materials,
 (f) covering said adhesive-coated surface with a release liner, and
 (g) cutting the resulting composite material across the width of the backing midway between adjacent pads whereby there are formed individual adhesive bandages comprising a central wound covering pad surrounded by an adhesive-coated backing.

10. A method of claim 9 wherein a medicinal or therapeutic composition is deposited centrally on said backing material prior to centering and securing said pad material to said backing material.

11. A method of claim 9 wherein said pad material is secured to said backing material and said portions of said pad and backing materials are compacted and heat-fused by compressing said bulky, nonwoven material while heated to about 100°–150° C.

12. A method of claim 9 wherein said nonwoven material comprises a mixture of absorbent fibers with at least 10% heat-fusible fibers.

13. A method of claim 12 wherein said heat-fusible fibers are staple length polyester core/polyethylene sheath conjugate fibers.

14. A method of claim 9 wherein said nonwoven material comprises a core of a mixture of absorbent fibers and heat-fusible polyester/polyethylene conjugate fibers, and an outer veneer on both faces of said core comprising a nonwoven web of heat-fusible polyester/polyethylene conjugate fibers.

15. A method of claim 14 wherein said absorbent fibers are selected from the group consisting of rayon, cotton, wood pulp, cotton linters, and mixtures thereof.

16. A method of claim 14 wherein the surface of said pad comprising a veneer of said heat-fusible fibers heat-glazed to impart nonsticking, wound release properties to said pad.

* * * * *